US010942118B2

(12) United States Patent
Maier et al.

(10) Patent No.: US 10,942,118 B2
(45) Date of Patent: Mar. 9, 2021

(54) MICROBIAL TEST STANDARD FOR USE IN INFRARED SPECTROMETRY

(71) Applicant: Bruker Daltonik GmbH, Bremen (DE)

(72) Inventors: Thomas Maier, Lilienthal (DE); Norman Mauder, Bremen (DE)

(*) Notice: Subject to any disclaimer, the term of this patent is extended or adjusted under 35 U.S.C. 154(b) by 155 days.

(21) Appl. No.: 15/955,289

(22) Filed: Apr. 17, 2018

(65) Prior Publication Data
US 2018/0306711 A1 Oct. 25, 2018

(30) Foreign Application Priority Data

Apr. 19, 2017 (DE) .................... 10 2017 108 278.6

(51) Int. Cl.
| | |
|---|---|
| G01N 21/3563 | (2014.01) |
| C12Q 1/04 | (2006.01) |
| G01N 1/31 | (2006.01) |
| G01N 1/38 | (2006.01) |
| G01N 21/27 | (2006.01) |
| G01N 21/31 | (2006.01) |
| G01N 21/35 | (2014.01) |
| G01N 1/28 | (2006.01) |

(52) U.S. Cl.
CPC ........... *G01N 21/3563* (2013.01); *C12Q 1/04* (2013.01); *G01N 1/312* (2013.01); *G01N 1/38* (2013.01); *G01N 21/278* (2013.01); *G01N 21/31* (2013.01); *G01N 21/35* (2013.01); *G01N 2001/2893* (2013.01); *G01N 2001/386* (2013.01); *G01N 2021/3572* (2013.01); *G01N 2021/3595* (2013.01)

(58) Field of Classification Search
None
See application file for complete search history.

(56) References Cited

U.S. PATENT DOCUMENTS

| 9,102,975 B2 | 8/2015 | Ben-David et al. |
| 2008/0132418 A1 | 6/2008 | Ismail et al. |
| 2010/0297092 A1* | 11/2010 | Farmer ................ A61K 35/742 |
| | | 424/93.46 |

(Continued)

FOREIGN PATENT DOCUMENTS

| CN | 102680425 A | 9/2012 |
| JP | H05296923 A | 11/1993 |

(Continued)

OTHER PUBLICATIONS

"Eppendorf Tubes," Product Manual, Eppendorf, 2015 (Year: 2015).*

(Continued)

*Primary Examiner* — David W Berke-Schlessel
(74) *Attorney, Agent, or Firm* — Benoit & Côté Inc.

(57) ABSTRACT

The invention relates to a microbial test standard for use in infrared spectrometry which has at least two resealable vessels which are liquid-tight when closed, each of which contains a predefined amount of dried biomass of a microorganism. The microorganisms in the different vessels differ in at least one characteristic, which is selected in particular from the group comprising species, subspecies, strain, serovar, pathovar, toxivar and variety, and the difference manifests itself in a predefined intermicrobial spectral distance. The disclosure furthermore comprises a method of using the microbial test standard.

15 Claims, 4 Drawing Sheets

(56) References Cited

U.S. PATENT DOCUMENTS

2011/0160594 A1  6/2011  Platsch et al.

FOREIGN PATENT DOCUMENTS

| | | |
|---|---|---|
| JP | 2010523970 A | 7/2010 |
| JP | 2010523970 A2 | 7/2010 |
| JP | 2012506026 A1 | 3/2012 |
| WO | 1999/016895 A1 | 4/1999 |
| WO | 2008/122975 A2 | 10/2008 |
| WO | 2010062356 A1 | 6/2010 |
| WO | 2013/093913 A1 | 6/2013 |
| WO | 2015/090727 A1 | 6/2015 |

OTHER PUBLICATIONS

"BD Falcon Tube and Pipets," Product Manual, BD Biosciences, 2011 (Year: 2011).*

Peiren, Jindrich et al., "Impact of the freeze-drying process on product appearance, residual moisture content, viability, and batch uniformity of freeze-dried bacterial cultures safeguarded at culture collections", Applied Microbiology and Biotechnology, Springer, DE, Bd. 100 Nt. 14 pp. 6239-6249, Feb. 15, 2016.

Naumann, Dieter "Infrared Spectroscopy in Microbiology" Encyclopedia of Analytical Chemistry (R.A. Meyers (Ed.), pp. 102-131, John Wiley & Sons Ltd, Cichester, 2000.

* cited by examiner

MICROBIAL TEST STANDARD FOR USE IN INFRARED SPECTROMETRY

BACKGROUND OF THE INVENTION

Field of the Invention

The invention relates to microbial (particularly bacterial) test standards for use in infrared spectrometry, especially in Fourier Transform Infrared Spectrometry (FTIR), preferably in transmission, as an aid and process control in measurements to differentiate, identify and/or characterize microorganisms.

Description of the Related Art

The prior art is explained below with reference to a special aspect. This shall not be understood as a limitation, however. Useful further developments and modifications of what is known from the prior art can also be used beyond the comparatively narrow scope of this introduction, and will easily be evident to experienced practitioners in the art in this field after reading the following disclosure.

IR spectra for microbial identification, which are preferably acquired in transmission, typically contain a number of extinction signals or absorption bands over a predefined range of wavelengths, especially in the mid-infrared region (approx. 4,000-400 $cm^{-1}$). As samples to be investigated, microorganisms provide clear and recognizable spectral signatures in these spectra. These signatures exhibit a superposition of contributions from all cell components, e.g. cytoplasmic components, membrane and cell wall components (i.e. particularly polysaccharides, DNA/RNA, proteins), and thus represent the phenotypic expression of the genome (DNA/RNA) or the genetic fingerprint. The character of this fingerprint forms the basis for using infrared spectrometry for the differentiation, identification and characterization of microorganisms. For particulars of these measurement methods, refer to the overview by Dieter Naumann "Infrared Spectroscopy in Microbiology" in the *Encyclopedia of Analytical Chemistry* (R. A. Meyers (Ed.), pp. 102-131, John Wiley & Sons Ltd, Chichester, 2000).

Nowadays, unforeseen and undesirable fluctuations and changes in instrument settings and properties of an infrared spectrometer over a certain period of operation, which could affect the reproducibility and comparability of measurements, can be detected and compensated for with some degree of reliability with the aid of automated test and recalibration routines.

However, the external measurement conditions can vary over an operating period, sometimes even from one acquisition to the next. Many infrared spectrometers are not equipped with conditioned sample support chambers which ensure constant and stable ambient conditions such as pressure, temperature and humidity during and between the individual acquisitions. It seems plausible that a change in humidity in particular can affect the spectral properties of a prepared sample, for example by forming hydration shells or water of crystallization, and thus can have a detrimental effect on the comparability of similar samples or even identical replicates. These differences would then become apparent particularly in the change between winter (cold air, low absolute humidity) and summer (warm air, high absolute humidity). There is therefore a need for better process monitoring in infrared spectrometry to better take account of these possible external effects and to assess IR measurements within a short period of time.

Simple forms of process control for IR measurements are already known. In the international application WO 99/16895 A1, for example, four batches of the microorganisms to be identified are each measured three times to monitor the spectral reproducibility, and then the similarity of these replicates with respect to each other is assessed.

An essential task of the differentiation, identification or characterization of microorganisms by means of IR spectrometry is to differentiate between strains and assess their phenotypic relationships with each other. The specific absorption spectra of microbial biomass are acquired and compared in order to determine the spectral distances with the aid of powerful cluster analysis algorithms and to visualize them so that the relationships become recognizable to the user. This presents the following challenges. On the one hand, high spectral specificity is required, particularly in order to distinguish between two different strains of the same microbial species; on the other hand, identical strains, even if they originate from different sampling points, have to reliably fall into the same cluster in the analysis, i.e. they must have the smallest possible intramicrobial spectral distances with respect to each other and among themselves in the replicates applied to the sample support in order for reliable reproducibility of the measurements to be achieved.

There is therefore a need to provide microbial test standards, and suitable methods to utilize them, with which the reproducibility and spectral specificity of the IR spectrometric measurement and the subsequent evaluation steps can be determined and assessed, when the identity and properties of the reference biomass measured are known.

SUMMARY OF THE INVENTION

According to a first aspect, the invention relates to a microbial test standard to be utilized in infrared spectrometry which has at least two resealable vessels which are liquid-tight when closed, each of which contains a predefined amount of dried biomass of a microorganism. The microorganisms in the different vessels differ in at least one characteristic, which can be selected in particular from the group comprising species, subspecies, strain, serovar, pathovar, toxivar and variety, and the difference manifests itself in a predefined intermicrobial spectral distance.

The test standard is preferably used in the following way. Together with the actual samples of unknown microorganisms, (at least) two reference microorganisms, which have a predetermined intermicrobial spectral distance from each other, are applied in duplicate or in a higher number of replicates onto the same sample support plate so as to be spatially separate. The reference biomasses are measured by means of IR spectrometry before the "real" samples which are to be identified.

To pass the test and designate the measurement of the sample support plate overall as valid, the intermicrobial spectral distances between the two reference microorganisms must be greater than a minimum spectral distance B in order to prove that the spectral specificity is sufficient. When applied in duplicate, four intermicrobial spectral distances can be calculated, each of which has to satisfy the condition in order to pass the test. If more than two replicates are applied per microorganism, for example five to ten, then instead of a 100% fulfillment condition being required, it is possible for a specific quantile of intermicrobial spectral distances, for example two to ten percent, preferably five percent, to deviate from the limit conditions without this leading to a test failure. 5×5 sample spots, for example, result in 25 intermicrobial spectral distances between the replicates of the two reference biomasses; a small number of deviations, for example one of these distances being less than B, could be tolerated without the measurement overall being designated as invalid.

Similar considerations naturally also apply in variants of this method for the intramicrobial maximum spectral distance A, given a correspondingly large number of applied replicates. To demonstrate a minimum degree of spectral reproducibility, the intramicrobial spectral distances of the replicates with respect to each other and among themselves, or at least a large quantile of them (>90%), shall be less than this specified maximum distance A.

Instead of labeling an IR measurement with a (warning) tag for a failed measurement, an experienced practitioner can also use the (partial) non-fulfillment of the test criteria to look at the IR spectra in detail and draw conclusions from this which allow the measurements to be repeated under modified and optimized conditions, if possible. For example, optimized humidity in the sample support chamber may lead to better results. If the signal-to-noise ratio of the absorption bands is too low, several acquisitions of the same sample spot can be added together to improve the database for the evaluation. Finally, the preparation of the microorganism samples on the sample support can also be examined to see whether they were applied with a largely uniform layer thickness. If this is not confirmed, the preparation can be repeated with particular attention being paid to this feature; and these optimization attempts can be monitored and checked with the microbial test standard.

Apart from the obvious taxonomic hierarchical levels of species and subspecies, an intermicrobial spectral distance can result from microorganisms having different detailed characteristics. The term "strain", for example, describes a population which was grown from a single organism and is kept at a (often state-run) depository for microorganism strains, with an internationally standardized strain designation being added to the nomenclature chain comprising genus, species, subspecies and type of variety. The individual organisms of a strain are genetically identical; different strains vary slightly in their genetic make-up, however, and thus provide a large variety of possible strain combinations with different spectral characteristics and distances, which can be suitable for utilization as a microbial test standard in IR spectrometry.

Other spectral specificities can express themselves in serotypes or serovars, for example. The term serotype or serovar (short for serological variant) is used to describe varieties within subspecies of bacteria which can be differentiated by means of serological tests. They differ in respect of the antigens on the surface of the cells and are identified in conventional microbiology with the aid of specific antibodies. The taxonomic hierarchy for serotypes is as follows: Genus>species>subspecies (subsp.)>serotype, for example with the full binomial species name *Salmonella enterica* subsp. *enterica* serotype *Typhi*, abbreviated to *Salmonella Typhi*.

A pathovar (from the Greek pathos "disease") is a bacterial strain or group of strains with the same characteristics, whose pathogenicity allows them to be differentiated from other strains within the species or subspecies. Pathovars are designated by means of a third or fourth addition to the binomial species name. The bacterium *Xanthomonas axonopodis*, for example, which can cause citrus canker, has various pathovars with different host specializations: *X. axonopodis* pv. *citri* is one of them. The abbreviation "pv." stands for "pathovar". The virulent strains of human pathogens also have pathovars, but in this case they are designated by prefixes before the name. The mostly completely harmless intestinal bacterium *Escherichia coli*, for example, has the highly dangerous pathovars enterohemorrhagic *E. coli* (EHEC), enteropathogenic *E. coli* (EPEC), enterotoxigenic *E. coli* (ETEC), enteroinvasive *E. coli* (EIEC), enteroaggregative *E. coli* (EAEC) and diffusely adherent *E. coli* (DAEC). The pathovars, in turn, can comprise different serotypes. With EHEC there are many known serotypes, around 60 percent of all identified EHEC serotypes being O157, O103 and O26. The serosubtype O157/H7 is particularly dangerous. It shall be understood that microorganisms which are harmless to humans are to be clearly preferred for microbial test standards in routine laboratory use.

In a broader sense, the microorganisms can also be divided up into varieties which differ in terms of other medically relevant characteristics, particularly their resistance to antibiotics (especially beta-lactam antibiotics and glycopeptide antibiotics), but also in their toxin formation ("toxivars") or their susceptibility to the same or similar bacteriophages ("phagovars"). In general, the term "biovars" is used if a selection of microbes of a species or subspecies have biological characteristics in common. One example of an antibiotic-resistant variety is MRSA: Methicillin-resistant *Staphylococcus aureus*.

The dried biomass can be sterilized to render it inert and thus protect against microbial contaminations which would falsify measurements; in particular, it can be in the form of vacuum-dried pellets. This form of preparation is particularly suitable for the fast processing of a test standard suspension to produce replicates on the sample support in the laboratory, when IR measurements are to be conducted quickly.

In a preferred embodiment, the microorganisms belong to different strains of one bacterial species. The species *Escherichia coli* shall be used by way of example, where the dried biomass in the different vessels can comprise the strains DH5α (DSM 6897) and ML3 (DSM 1058) in a particularly preferred embodiment. Two bacterial strains allow a defined intermicrobial spectral distance to be determined in order to thus monitor and assess the reproducibility between the replicates of a strain and the spectral specificity between the individual measurements of the different strains. It is particularly advantageous when the strains occur regularly in microbial samples and are therefore of sufficient practical relevance; this is the case with *E. coli* strains. The intermicrobial spectral distance can manifest itself as a distance between two principal components of a principal component analysis. In further preferred embodiments, the spectral distance can also be Euclidian, which corresponds to the difference in the n-dimensional spectral vectors. Depending on the resolution or the selected wave number range, the dimensionality can start in the two-digit range and extend to several hundred or more, for example $20<n<2,000$, particularly $400<n<600$, for example $n=500$.

The vessels can have screw caps for secure opening and resealing. Even after a solvent has been added to the vessels to process a suspension of microorganisms, the suspension can be stored over a long period (e.g. up to ten weeks) for further utilization without the informative value of the spectra acquired therefrom being adversely affected.

According to a second aspect, the invention relates to the utilization of such a microbial test standard, comprising:— Provision of a sample support for infrared spectrometry which has an array of sample spots, typically 48, 96 or 384 in matrix row-column arrangement; —Re-suspension of the biomass in the vessels by adding a solvent, for example distilled and/or deionized water; —Extraction of a predetermined quantity of the suspension from each vessel, which is then deposited on a predetermined number of sample spots, preferably in duplicates or triplicates; —Drying of the suspension on the sample spots, where appropriate with the aid of heat and convection; —Acquisition of infrared spectra of the sample spots, preferably in transmission; —Calculation of intermicrobial spectral distances between spectral signatures in the infrared spectra of the different sample spots; and—Determination of whether the spectral distances are outside a predetermined range. If this is the case, the IR spectra of the sample support overall can be labeled with a corresponding (warning) tag.

In different embodiments, the spectral distances in a predetermined range of wave numbers, preferably between around 1,300 and 800 $cm^{-1}$ to reduce the effect of interfering water absorption bands, can be computed from the microbial spectral signatures, and they can correspond to a predetermined distance, for example the Euclidian distances of the spectral vectors directly. An analysis of a larger number of spectra could also be carried out here with the aid of a hierarchical cluster analysis (HCA). Or the computation is carried out by means of a principal component analysis of the microbial spectral signatures, and the distances then correspond to a predetermined distance in the principal component space. Alternative procedures to differentiate different microorganisms, drawn from the field of supervised machine learning, are, for example, ANN (artificial neural network analysis), PLS-DA (partial least-square discriminant analysis) and SVM (support vector machines). In these cases, however, it is not the spectral distances which are of crucial importance, but the correct assignment of the test spectra to the expected classes.

In addition to the intermicrobial distances, it is also possible to compute intramicrobial spectral distances (i.e. distances between replicates of the same microorganism) between the spectral signatures in the infrared spectra of the different sample spots for the purpose of examining the spectral reproducibility.

It is preferable (i) for the predetermined range of the intramicrobial spectral distance to extend up to a maximum distance A, which is a measure for the reproducibility of the acquisitions, and (ii) for the predetermined range of the intermicrobial spectral distance to extend from a minimum distance B, which is a measure for the spectral specificity in the acquisitions. In various embodiments, a small number (e.g. two to ten percent, particularly five percent) of spectral distances between the IR spectrometric acquisitions of the different, individual sample spots can fail to fulfill the distance conditions without such a finding leading to a negative tagging or even a declaration that all measurements from this sample support are invalid, provided that a significant majority of the distances do fulfill them.

Re-suspension, in the sense of a uniform distribution of the suspended microorganism cells, can be promoted by agitating the vessels. Vessels with screw caps, in particular, guarantee that the surroundings are reliably safeguarded against the unintended escape of microbial aerosols and are suitable for storing the remaining suspension for a period of weeks for later use. If need be, mix-pipetting can be used additionally or alternatively to promote the re-suspension when the vessel is open.

In various embodiments, the storage life of the suspension can be extended by adding ethanol. After such a measure, the prepared suspensions can be stored for several weeks, particularly up to ten weeks, for later use in measurement monitoring and process control.

It is particularly practicable to evaluate the infrared spectra by using a Fourier transform, because unknown recurrent extinction signals can thus be detected with a high degree of sensitivity.

BRIEF DESCRIPTION OF THE DRAWINGS

The invention can be better understood by referring to the following illustrations. The elements in the illustrations are not necessarily to scale, but are intended primarily to illustrate the principles of the invention (mainly schematically). In the illustrations, the same reference numbers designate corresponding elements in the different views.

DETAILED DESCRIPTION

While the invention has been illustrated and explained with reference to a number of different embodiments thereof, those skilled in the art will acknowledge that various changes in form and detail may be made to it without departing from the scope of the technical teaching as defined in the appended claims.

The dried biomass for the microbial IR test standard can be produced in the following way: The different reference microorganisms are cultured overnight on a two-dimensional culture medium (e.g. Columbia sheep blood agar). The cultured cells are inoculated into several hundred milliliters of nutrient broth (e.g. LB—lysogeny broth) before they are allowed to grow again at 37° C. with slight agitation of a few hundred rpm for several hours (e.g. 12 to 24 hours). The broth thus enriched can then be divided between a number of centrifuge vessels and centrifuged at several thousand g for several minutes. The supernatant is disposed of, and the microbial pellet left behind is re-suspended in water to remove the residual nutrient broth. Renewed centrifugation and renewed re-suspension in water, supplemented by the addition of a protic solvent such as ethanol, if necessary, produce a suspension whose microorganism content can be determined by measuring the optical density (e.g. in accordance with the McFarland standard). If the concentration of the suspended microorganisms is sufficient, the suspension can be aliquoted into plastic vessels and dried therein, for example in a vacuum at slightly raised temperatures, in order to form a ready-to-use pellet, from which the liquid has been removed, in the vessel itself.

Figure 1A:
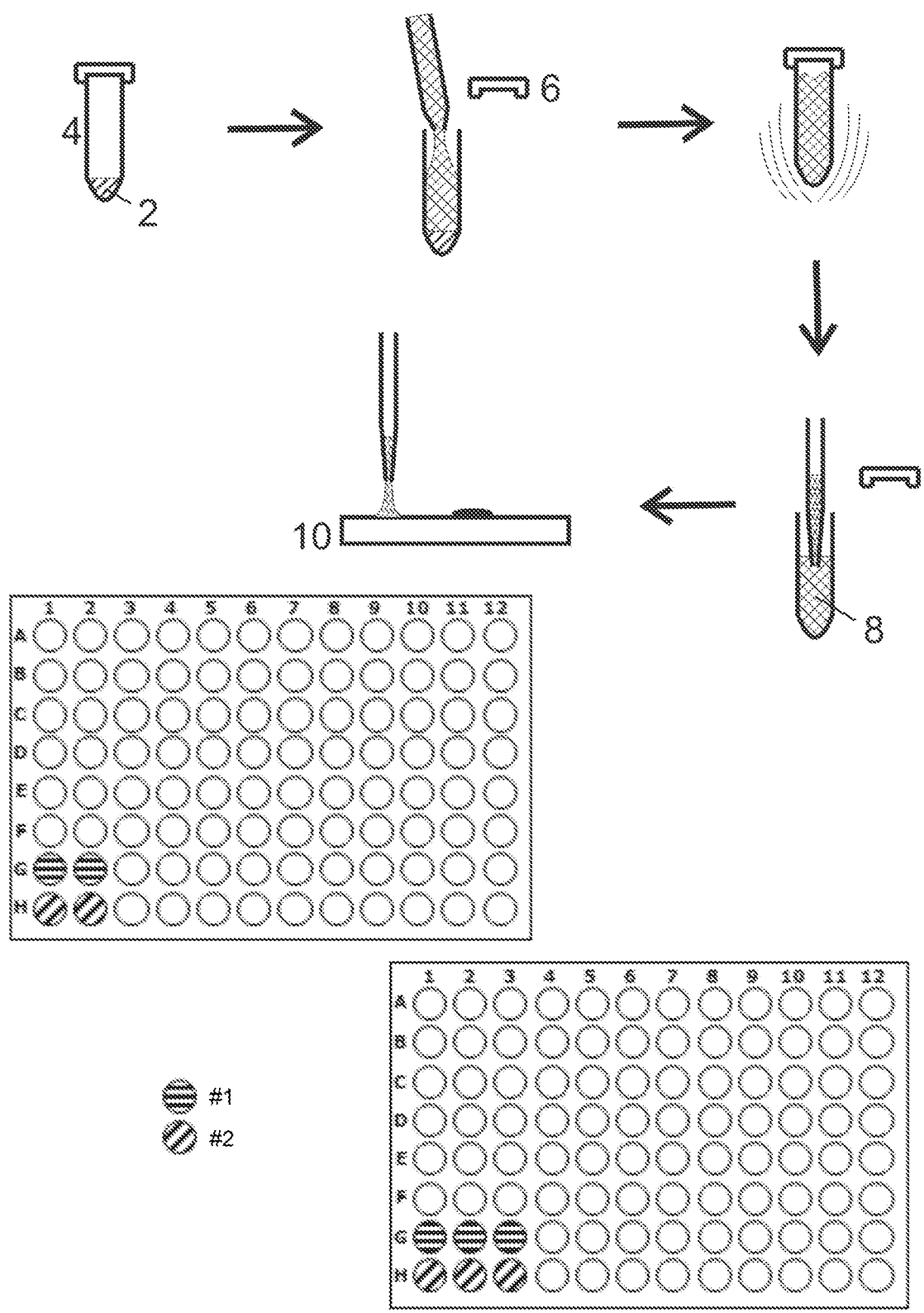
FIG. 1A is a schematic representation of the first part of an example use of a microbial test standard.
Figure 1B:
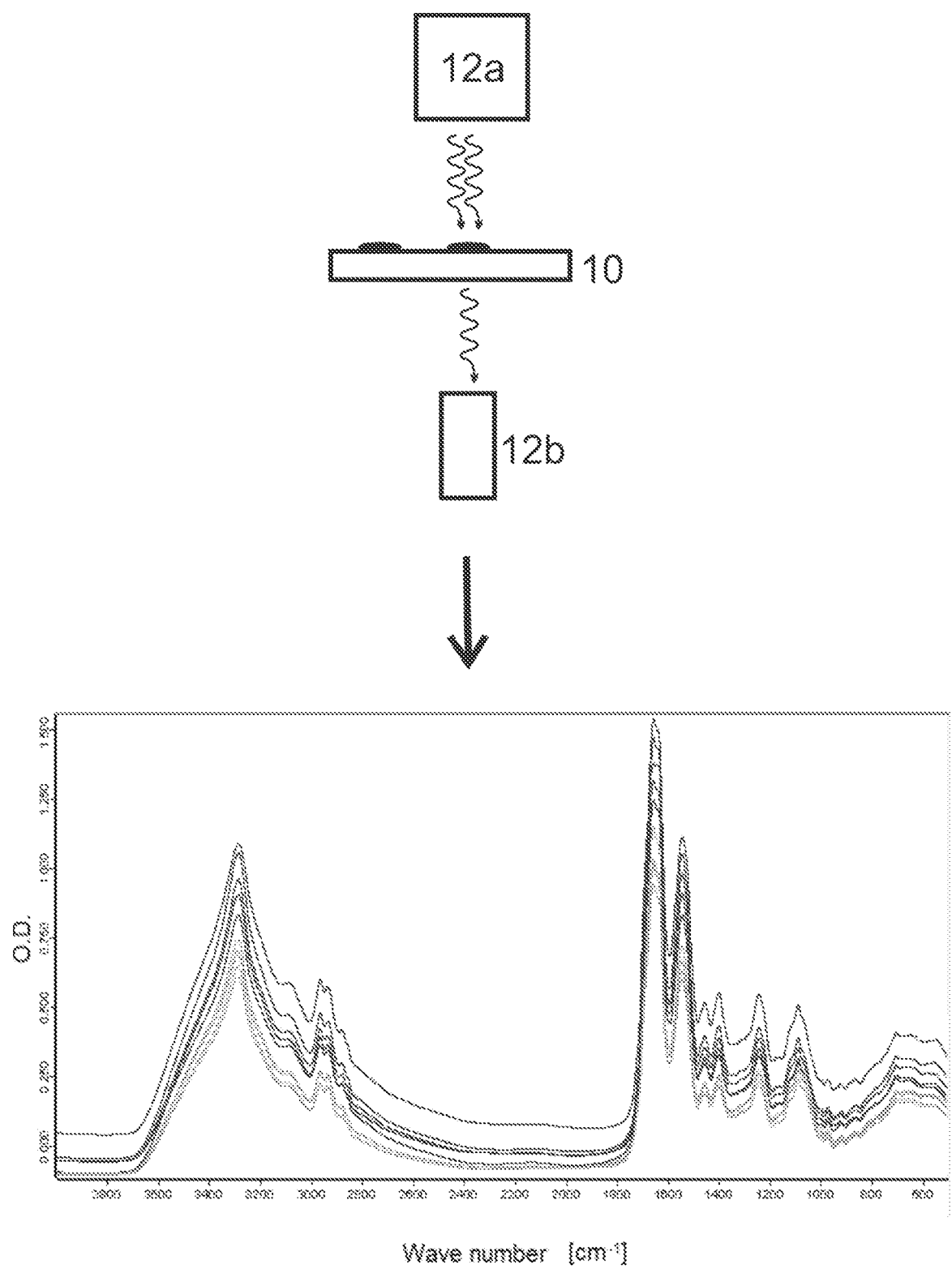
FIG. 1B provides a schematic illustration of an IR spectrometric measurement in transmission through dried samples with corresponding example of an extinction spectrum.
Figure 1C:
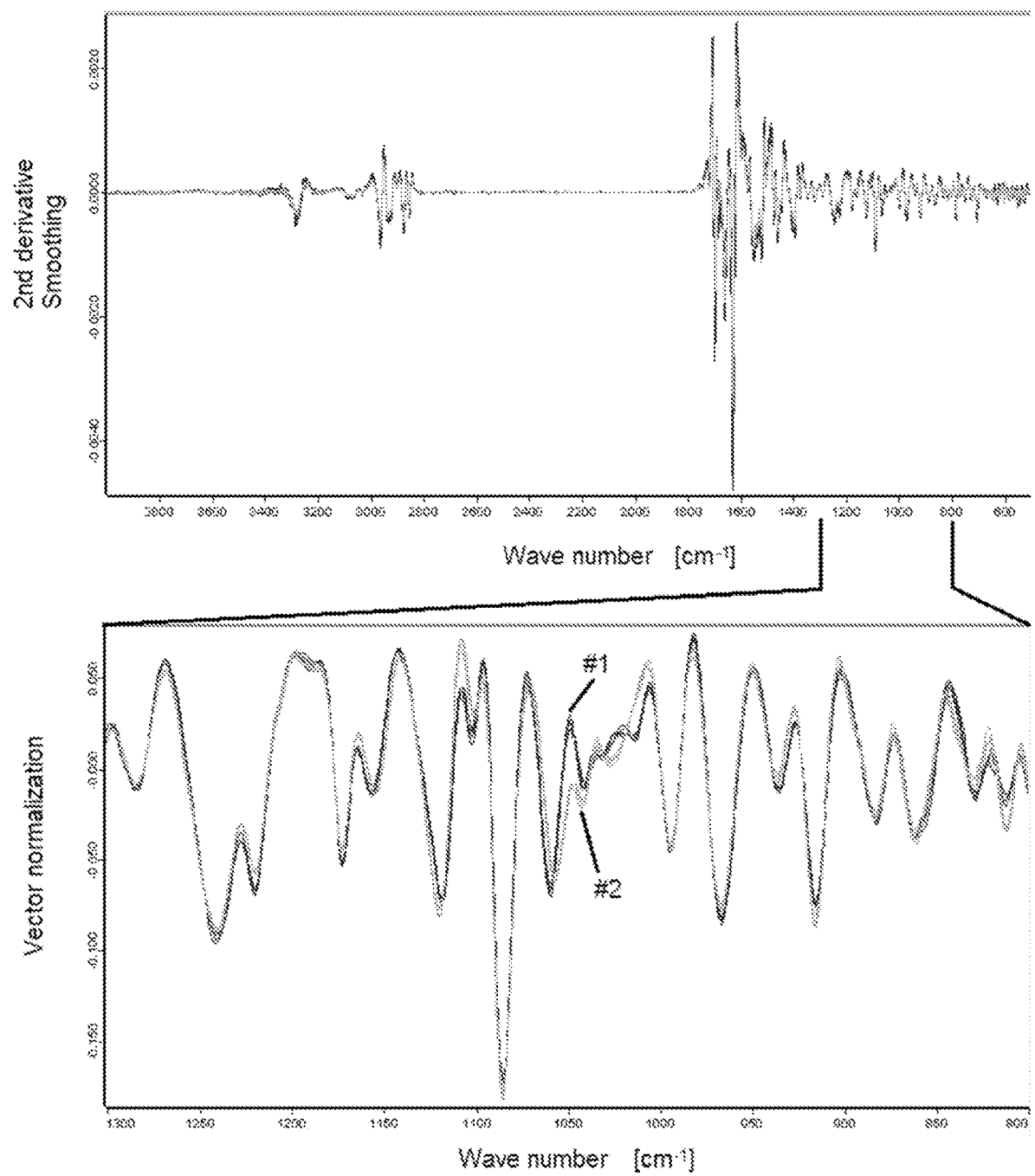
FIG. 1C gives a schematic illustration of the different processing steps of an extinction spectrum which are carried out before the evaluation.

FIGS. 1A to 1C outline a possible procedure for using a microbial test standard.

The dried biomass (2) for the two reference microorganisms can be supplied in plastic containers (4) with screw caps (6). To prepare a reference sample, the screw cap (6) is removed and a quantity of solvent such as distilled or de-ionized water is added to re-suspend the dry pellets (2). After the vessels (4) have been resealed, this procedure can be assisted by light shaking or, additionally or alternatively, by repeatedly drawing liquid into a pipette tip and forcing it out again ("mix-pipetting") without forming any bubbles (not shown).

After a few minutes, when the solid biomass has "dissolved" and is no longer visible, the caps (6) can be removed again and a quantity of the microbial suspension (8) removed from the vessels (4) and applied to a number of sample spots (A-H; 1-12) on an IR spectrometry sample support (10). This can be done in duplicates, triplicates or a larger number of replicates, as is shown schematically for two sample supports (10) with a 96 sample spot array (eight rows A-H, twelve columns 1-12). In general, the statistical basis of the spectral distance determination can be improved by increasing the number of replicates of the test standard, but only at the expense of a correspondingly smaller number of sample spots for the analytical samples that are actually to be identified on the sample support. The latter are not shown here for reasons of clarity. The droplets of the test standard suspension are dried, assisted where necessary by thermal irradiation at a temperature slightly higher than room temperature and/or a stream of air.

The microorganisms of the reference standard (#1, #2) are then measured in the same run as the actual sample with an IR spectrometer (12a, 12b), preferably in transmission, as shown. One example for such a spectrometer is the TENSOR II FTIR from Bruker Optik GmbH. The result of such a measurement is an extinction spectrum, as shown at the bottom of FIG. 1B by way of example. The optical density (O.D.) is plotted as a function of the wave number, as is usual in spectrometry. The spectra acquired are differentiated twice and smoothed in each case over a specific number of data points. A wave number range is then chosen in which the absorption bands of microbial cells, which are caused in particular by carbohydrates and proteins, stand out best with respect to background effects, such as water absorption bands, and therefore provide the best signal-to-background ratio. The range between around 1,300 and 800 $cm^{-1}$ is particularly suitable for this; FIG. 1C.

A vector normalization prepares the selected spectral range for the subsequent evaluation with regard to the spectral distance measures. One option to determine the spectral distance from the microorganism-specific extinction signals is a principal component analysis. The crucial issue here is that the microorganisms for the different vessels are selected such that they can be represented in different components with reliable, slight but clear differences. Although the intermicrobial spectral distance is defined essentially by a lower limit, it should not be set too high in order to enable an assessment to be made about the spectral specificity at the performance limit of the infrared spectrometer. Nor should it be too low in order to counteract the danger of a variance-induced, random overlapping of the principal component data clouds, which exhibit a certain variance from measurement to measurement.

Figure 2:
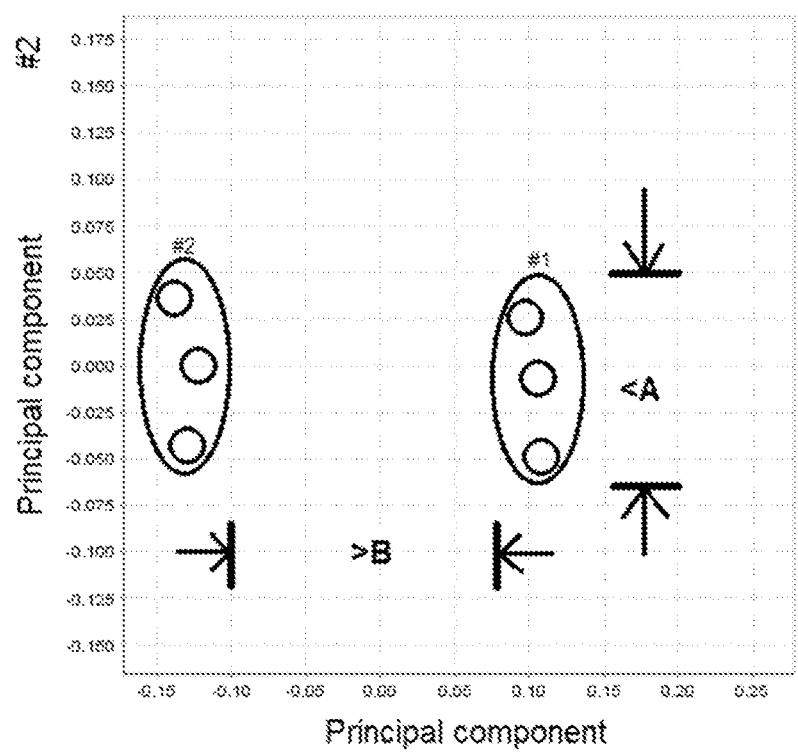
FIG. 2 provides a schematic illustration of the possible result of a spectral distance determination for replicates of two bacterial strains in a two-dimensional principal component space.

FIG. 2 is a schematic representation, by way of example, of a result of a principal component analysis on the basis of IR spectra of two bacterial strains. The intramicrobial spectral distance between the replicates of the same microorganism must not exceed a certain peak value A, because then it would not be possible to confirm the identity, which would cast doubt on the quality of the measurement. In addition, the intermicrobial spectral distance between the different replicates of the different microorganisms used must not fall below a certain lower limit B, because then the spectral specificity of the measurement was not sufficient. The larger the number of replicates of the individual microorganism suspensions, the more statistically reliable the assessments derived from them. However, the space available for the actual microbial measuring samples on the sample support has to be taken into account.

As can be seen in FIG. 2, two separate data clouds, shown in outline, form in the two-dimensional principal component space when the same microorganisms are measured again. These clouds are in close proximity to each other with regard to the individual replicates of one organism, but are a significant distance from the replicates of the other organism in each case (in the example shown>0.15 arbitrary units). Since the microbial test standard is investigated in the same measurement run as the real microbial samples, this distance in the computed principal components allows an assessment to be made about the spectral specificity of the IR spectrometer. At the same time, the reproducibility of the IR measurement can be assessed by means of the intramicrobial spectral distances of the individual replicates of the same microorganism with respect to each other and among themselves. If individual data points from the replicates of the same organism exceed the maximum permissible distance A, this would be regarded as an indication of a problem with the reproducibility of the measurements. The parallel measurements of real samples can then be tagged accordingly. If it is even the case that the data clouds of the different microorganisms spill over into each other, the spectral specificity would not be adequate. This reduces the quality of the identification, and it may even be necessary to label the identification/characterization result from the sample support in question as unreliable under the given measurement conditions.

The use of a principal component analysis above shall not be understood as a limitation, but as an illustrative example. Principles of the present disclosure can also be carried out with alternative methods of determining spectral distances, for example with the native Euclidian distances and/or with the aid of hierarchical cluster analyses. The test spectra could also be classified with ANN (artificial neural network analysis) appropriately trained in advance, PLS-DA (partial least-square discriminant analysis), or SVM (support vector machines).

Above, the principles of the invention have been explained with the aid of two spectrally distinguishable microorganisms. Those skilled in the art will recognize, however, that more than two suitable microorganisms can also be used to provide a microbial test standard for infrared spectrometry. The fundamental idea can be expanded as desired in this respect.

The invention has been described above with reference to different, specific example embodiments. It is understood, however, that various aspects or details of the embodiments described can be modified without deviating from the scope of the invention. In particular, characteristics and measures disclosed in connection with different embodiments can be combined as desired if this appears practicable to a person skilled in the art. Moreover, the above description serves only as an illustration of the invention and not as a limitation of the scope of protection, which is exclusively defined by the appended claims, taking into account any equivalents which may possibly exist.

The invention claimed is:

1. A method of evaluating a spectral specificity of an infrared (IR) spectrometric measurement, the method comprising:
    providing a microbial test standard having at least two resealable vessels which are liquid-tight when closed, each of which contains a predefined amount of dried biomass of a microorganism, wherein the microorganisms in the respective vessels differ in at least one characteristic that manifests itself in a predefined spectral distance between spectral signatures in infrared spectra of the respective biomasses;

combining each biomass with a solvent to produce first and second biomass suspensions;

applying a predetermined quantity of each suspension to a different sample spot of an infrared spectrometry sample support plate;

drying each of the suspensions on the sample support plate and acquiring infrared spectra of the sample on each sample spot;

measuring the spectral distances between spectral signatures of the infrared spectra acquired from the samples; and comparing the measured spectral distances to the predefined spectral distance and identifying the measurement as meeting a satisfactory performance limit if said measured spectral distances are within a predetermined range relative to the predefined spectral distance.

2. The method according to claim 1, wherein the at least one characteristic is selected from the group: species, subspecies, strain, serovar, pathovar, toxivar and variety.

3. The method according to claim 1, wherein the dried biomass is comprised of vacuum-dried pellets.

4. The method according to claim 1, wherein the microorganisms belong to different strains of one bacterial species.

5. The method according to claim 1, wherein the vessels have screw caps.

6. A method of evaluating a validity of an infrared spectrometric measurement of samples on an infrared spectrometry sample support having an array of sample spots on which are deposited analytical samples with unknown infrared spectral properties, the method comprising:

providing a microbial test standard having at least two resealable vessels which are liquid-tight when closed, each of which contains a predefined amount of dried biomass of a microorganism, wherein the microorganisms in the respective vessels differ in at least one characteristic that manifests itself in a predefined spectral distance between spectral signatures in infrared spectra of the respective biomasses;

combining each biomass with a solvent to produce first and second biomass suspensions, applying a predetermined quantity of each of the first and second suspensions to a different one of the sample spots of the sample support and drying of the suspensions to form microbial test standard sample spots, acquiring infrared spectra from the microbial test standard sample spots;

acquiring infrared spectra from the analytical sample spots;

measuring spectral distances between spectral signatures in the infrared spectra of the different microbial test standard sample spots;

comparing the measured spectral distances to the predefined spectral distance to determine whether said measured spectral distances are within a predetermined range relative to the predefined spectral distance; and identifying infrared spectra from the analytical samples on the sample support as being invalid measurements if said measured spectral distances are not within said predetermined range.

7. The method according to claim 6, wherein the measured spectral distances are computed from the microbial spectral signatures in a predetermined wave number range and correspond to a predetermined distance.

8. The method according to claim 7, wherein the predetermined wave number range is between around 1,300 and 800 cm$^{-1}$.

9. The method according to claim 6, wherein the spectral distances between the spectral signatures of the infrared spectra of the different microbial test standard sample spots are computed to examine the spectral reproducibility.

10. The method according to claim 9, wherein the predetermined range extends to a maximum distance A, which is a measure for the reproducibility of the acquired infrared spectra, and extends from a minimum distance B, which is a measure of spectral specificity in the acquisitions.

11. The method according to claim 6, wherein the solvent for the re-suspension contains distilled and/or deionized water.

12. The method according to claim 6, wherein each biomass is combined with the solvent in its respective vessel, and wherein the method further comprises mixing each biomass with the solvent by agitating the vessels or by mix-pipetting.

13. The method according to claim 6, wherein a plurality of replicates of the microorganism suspensions are applied to the sample support.

14. The method according to claim 1, wherein the dried biomass is sterilized.

15. The method according to claim 1, wherein the microorganisms are taken from the species *Escherichia coli* and the dried biomass in the different vessels comprises the strains DH5a (DSM 6897) and ML3 (DSM 1058).

* * * * *